(12) United States Patent
Hotte et al.

(10) Patent No.: US 9,885,011 B2
(45) Date of Patent: Feb. 6, 2018

(54) V-SHAPED LIGHT DISTRIBUTOR SYSTEM

(71) Applicants: CENTRE DE RECHERCHE INDUSTRIELLE DU QUÉBEC, Québec (CA); INSTITUT NATIONAL D'OPTIQUE, Québec (CA)

(72) Inventors: Denis Hotte, L'Ancienne-Lorette (CA); Marc-André Boucher, Lac-Beauport (CA); Marc Daigle, Québec (CA); Paul Grenier, Québec (CA); Frédéric Lamontagne, Québec (CA); Yann Le Bihan, Québec (CA); Marc Lévesque, Saint-Augustin-de-Desmaures (CA)

(73) Assignees: INSTITUT NATIONAL D'OPTIQUE, Québec (CA); CENTRE DE RECHERCHE INDUSTRIELLE DU QUÉBEC, Québec (CA)

( * ) Notice: Subject to any disclaimer, the term of this patent is extended or adjusted under 35 U.S.C. 154(b) by 140 days.

(21) Appl. No.: 14/894,353

(22) PCT Filed: May 28, 2014

(86) PCT No.: PCT/IB2014/061790
§ 371 (c)(1),
(2) Date: Nov. 26, 2015

(87) PCT Pub. No.: WO2014/191939
PCT Pub. Date: Dec. 4, 2014

(65) Prior Publication Data
US 2016/0113212 A1 Apr. 28, 2016

Related U.S. Application Data

(60) Provisional application No. 61/828,224, filed on May 29, 2013.

(51) Int. Cl.
*C12M 1/00* (2006.01)
*A01G 7/00* (2006.01)
(Continued)

(52) U.S. Cl.
CPC .............. *C12M 21/02* (2013.01); *A01G 7/00* (2013.01); *A01G 9/20* (2013.01); *A01G 9/243* (2013.01);
(Continued)

(58) Field of Classification Search
CPC .......... C12M 21/02; F24J 2/5267; F24J 2/541
See application file for complete search history.

(56) References Cited

U.S. PATENT DOCUMENTS 4,088,121 A  5/1978 Lapeyre
4,153,039 A  5/1979 Carroll
(Continued)

FOREIGN PATENT DOCUMENTS

WO  2004074423  9/2004
WO  2011099016  8/2011

OTHER PUBLICATIONS

Zijffers et al., Design Process of an Area-Efficient Photobioreactor, Mar Biotechnol, Feb. 2008, pp. 404-415, Spinger.

*Primary Examiner* — Avinash Savani
*Assistant Examiner* — Deepak Deean

(57) ABSTRACT

A sun-tracking light distributor for a photosynthetic culture in an aqueous liquid, comprising: two light distribution walls made of a transparent material, creating an elongated V-shaped channel adapted to receive the sunlight and to be partly immersed in the aqueous liquid, the sun-tracking light distributor has a center of buoyancy, a vertical passing through the center of buoyancy defines an axis of flotation, and a pivot axis of the sun-tracking light distributor is offset relative to the axis of flotation. Owing to the offset pivot (Continued)

axis, the orientation of the light distributor is changed by varying the level of aqueous liquid, thus allowing a tracking of the sun's altitude.

8 Claims, 12 Drawing Sheets

(51) Int. Cl.
  *A01G 9/24* (2006.01)
  *A01G 9/20* (2006.01)
  *C12N 1/12* (2006.01)
  *F24J 2/52* (2006.01)
  *F24J 2/54* (2006.01)

(52) U.S. Cl.
  CPC ............. *C12N 1/12* (2013.01); *F24J 2/5267* (2013.01); *F24J 2/541* (2013.01); *F24J 2002/5437* (2013.01); *Y02P 60/124* (2015.11)

(56) References Cited

U.S. PATENT DOCUMENTS

| | | | |
|---|---|---|---|
| 4,194,949 A | 3/1980 | Stark | |
| 4,210,121 A | 7/1980 | Stark | |
| 4,300,530 A * | 11/1981 | Tetirick | F24J 2/0494 126/568 |
| 4,315,500 A * | 2/1982 | Gonder | F24J 2/07 126/561 |
| 4,350,143 A * | 9/1982 | Laing | C02F 1/14 126/567 |
| 4,626,065 A | 12/1986 | Mori | |
| 4,952,511 A | 8/1990 | Radmer | |
| 5,581,447 A | 12/1996 | Raasakka | |
| 5,981,271 A | 11/1999 | Doucha et al. | |
| 6,037,535 A | 3/2000 | Yoshino | |
| 7,642,450 B2 * | 1/2010 | Connor | F24J 2/085 126/573 |
| 7,813,061 B2 | 10/2010 | Steneby | |
| 7,891,351 B2 * | 2/2011 | Hinderling | F24J 2/07 126/565 |
| 7,980,024 B2 * | 7/2011 | Berzin | C12M 21/02 435/289.1 |
| 8,033,047 B2 | 10/2011 | Rasmussen et al. | |
| 8,184,372 B1 | 5/2012 | Gu | |
| 8,307,820 B2 * | 11/2012 | King | F24J 2/0015 126/571 |
| 8,443,615 B2 * | 5/2013 | King | F24J 2/0015 62/115 |
| 8,650,798 B1 | 2/2014 | Armstrong et al. | |
| 9,201,228 B1 | 12/2015 | Steinmeyer et al. | |
| 2005/0034644 A1 * | 2/2005 | Hamm | E02B 3/064 114/44 |
| 2006/0191566 A1 | 8/2006 | Schaafsma | |
| 2008/0268302 A1 | 10/2008 | McCall | |
| 2008/0311649 A1 | 12/2008 | Cloud et al. | |
| 2009/0148931 A1 | 6/2009 | Wilkerson et al. | |
| 2009/0291485 A1 | 11/2009 | Shigematsu et al. | |
| 2009/0305389 A1 | 12/2009 | Wilson et al. | |
| 2010/0028991 A1 | 2/2010 | McCall | |
| 2010/0170149 A1 | 7/2010 | Keeler et al. | |
| 2010/0186733 A1 * | 7/2010 | Hoefler | F24J 2/055 126/625 |
| 2010/0212655 A1 | 8/2010 | Henkel-Wallace et al. | |
| 2010/0216203 A1 | 8/2010 | Trent et al. | |
| 2010/0248333 A1 | 9/2010 | Bartilson | |
| 2011/0070632 A1 * | 3/2011 | Katoch | B08B 1/008 435/286.6 |
| 2011/0070635 A1 * | 3/2011 | King | F24J 2/0015 435/292.1 |
| 2011/0117631 A1 | 5/2011 | Woerlee et al. | |
| 2011/0117632 A1 | 5/2011 | Woerlee et al. | |
| 2011/0153087 A1 | 6/2011 | Cohen et al. | |
| 2011/0197317 A1 | 8/2011 | Wong | |
| 2011/0217764 A1 * | 9/2011 | Christenson | C12M 1/10 435/289.1 |
| 2012/0021507 A1 * | 1/2012 | Hui | C12M 27/04 435/325 |
| 2012/0234668 A1 * | 9/2012 | King | F24J 2/0015 204/157.5 |
| 2013/0029403 A1 | 1/2013 | Hazlebeck et al. | |
| 2013/0219781 A1 * | 8/2013 | Levesque | F21S 11/005 47/1.4 |
| 2013/0323713 A1 * | 12/2013 | Levesque | C12M 41/08 435/3 |
| 2015/0226462 A1 * | 8/2015 | Tennler | F24J 2/38 126/608 |

\* cited by examiner

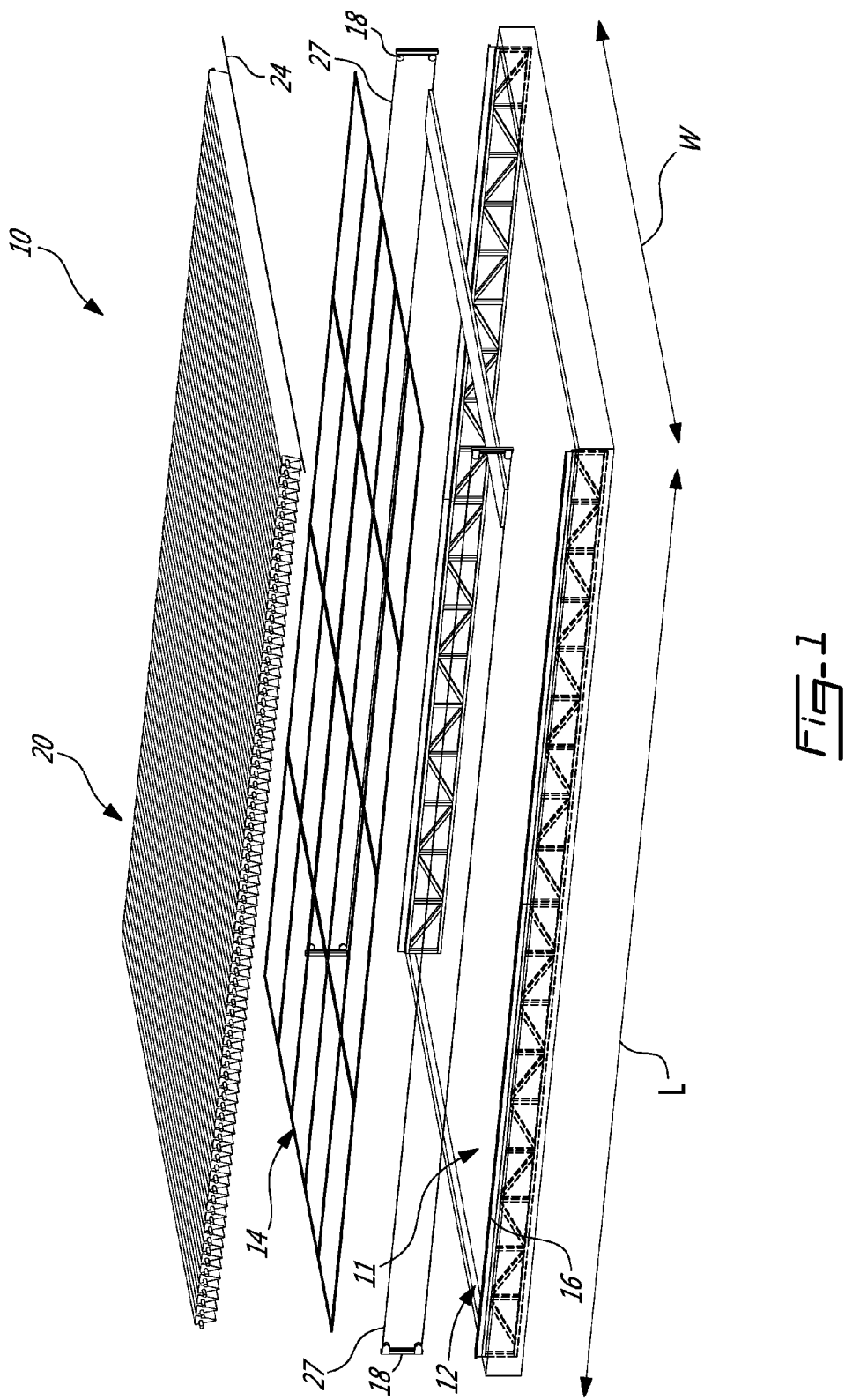

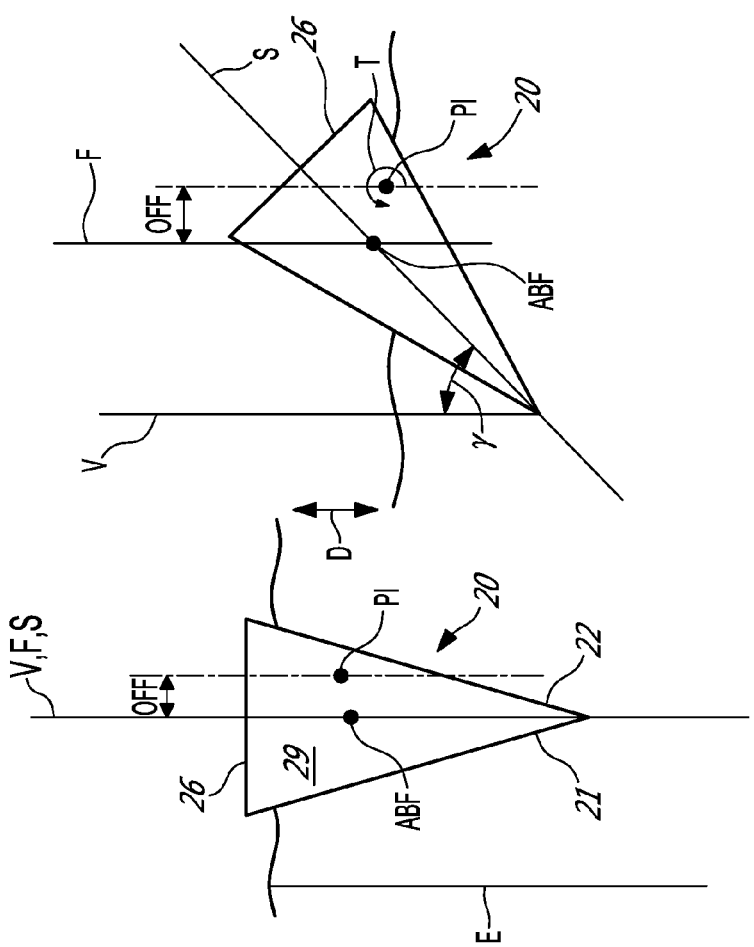

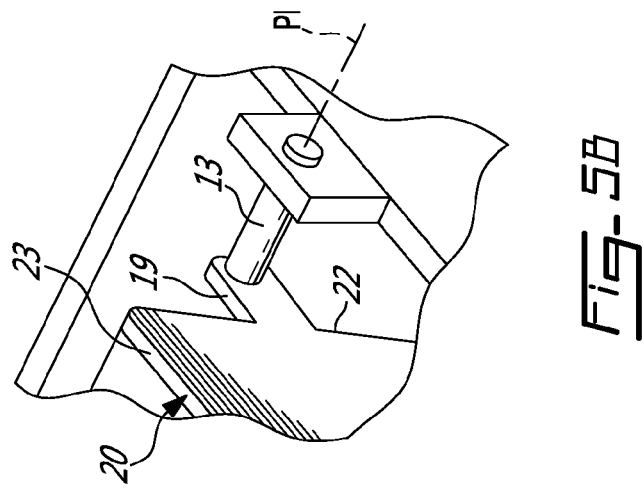
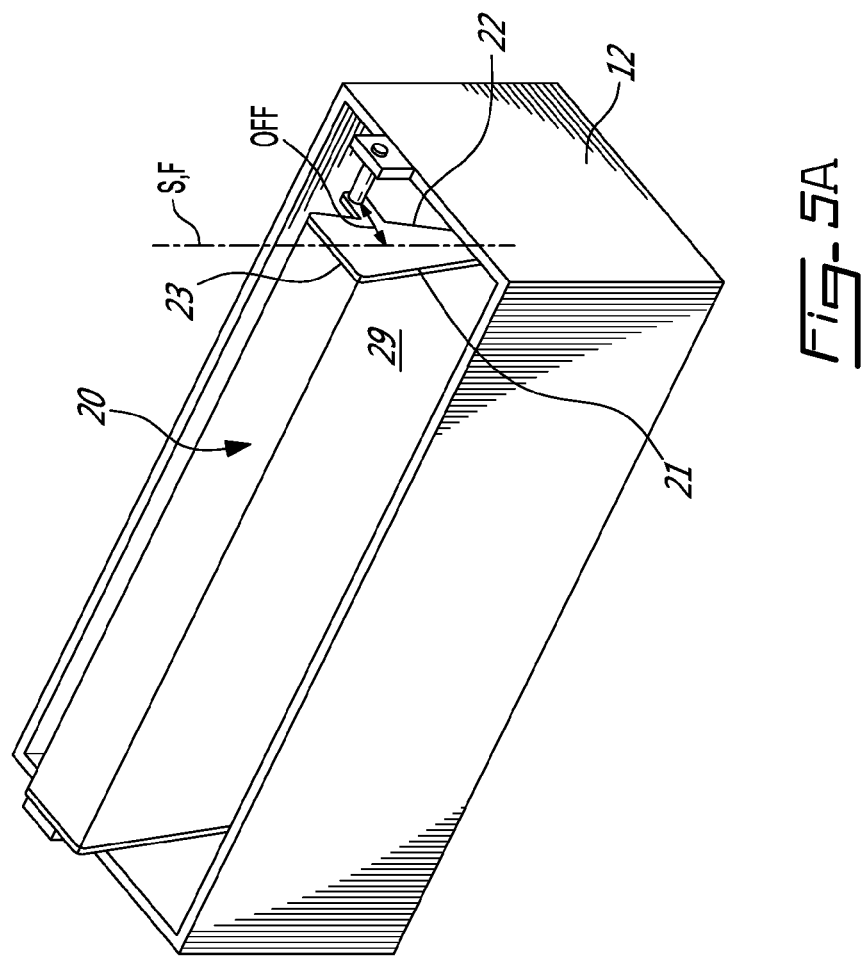

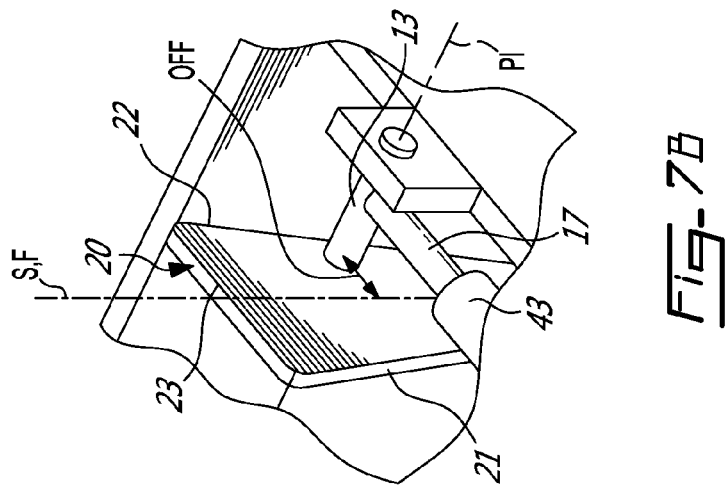
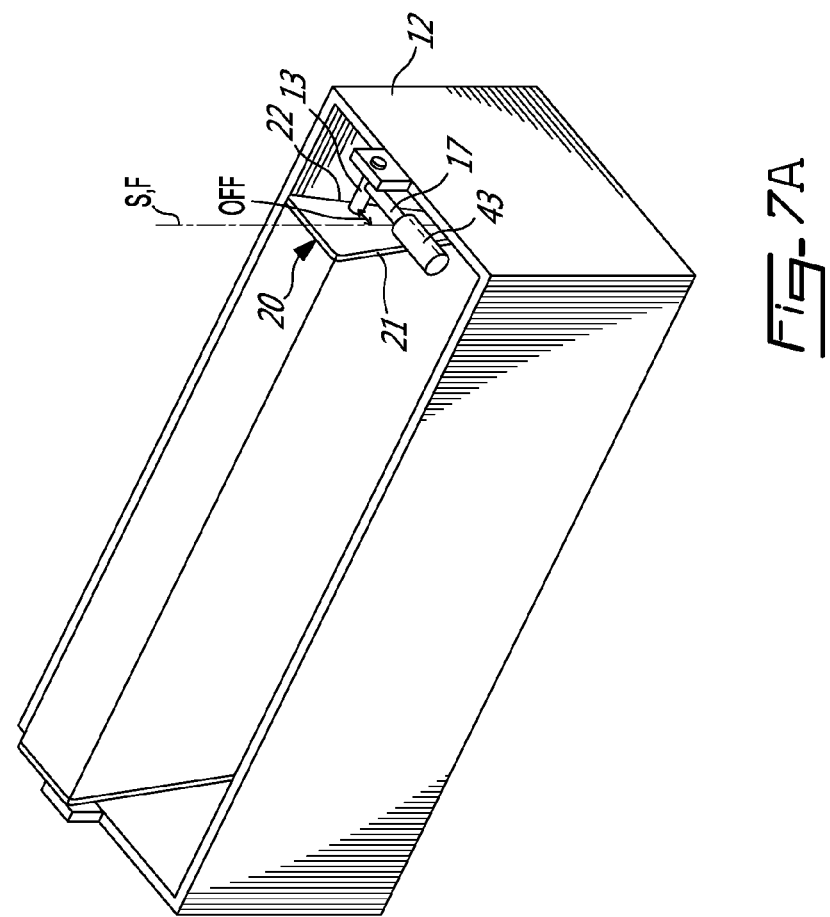

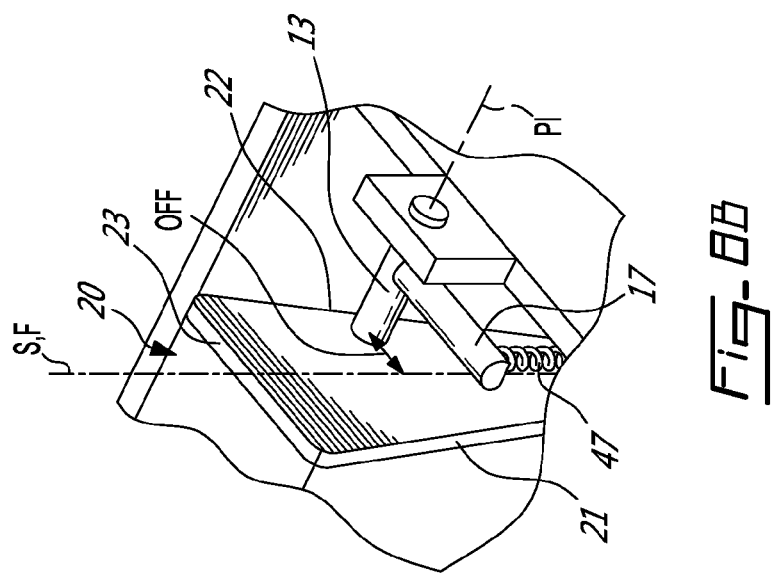
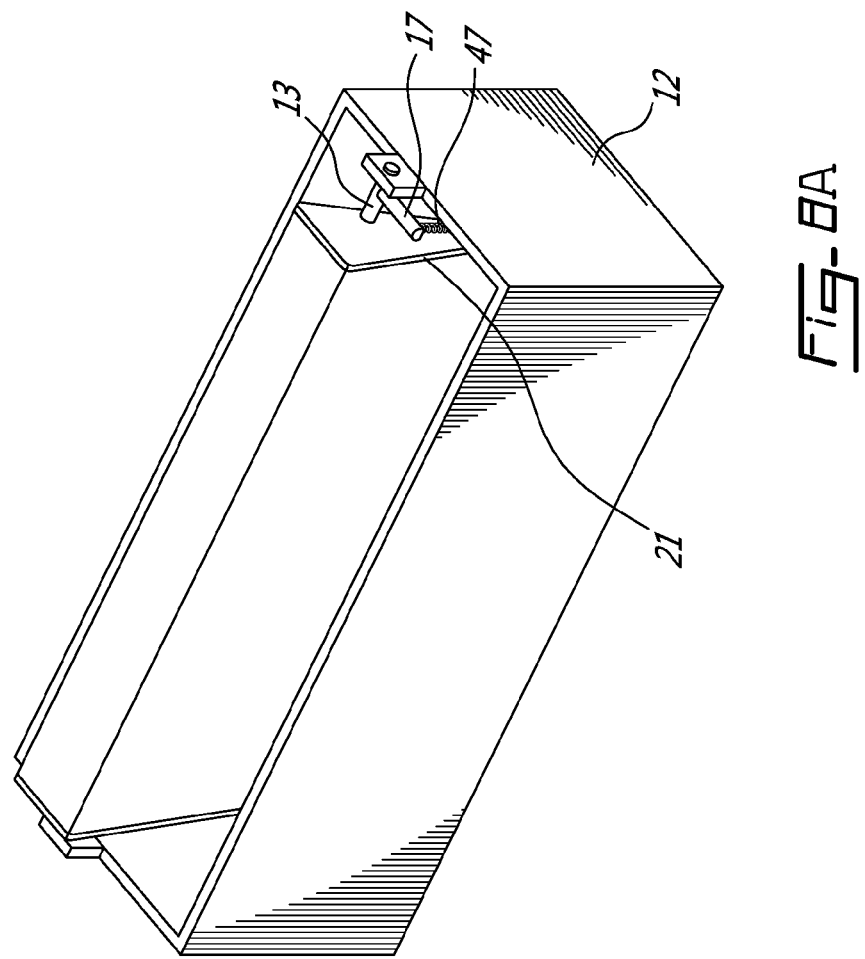

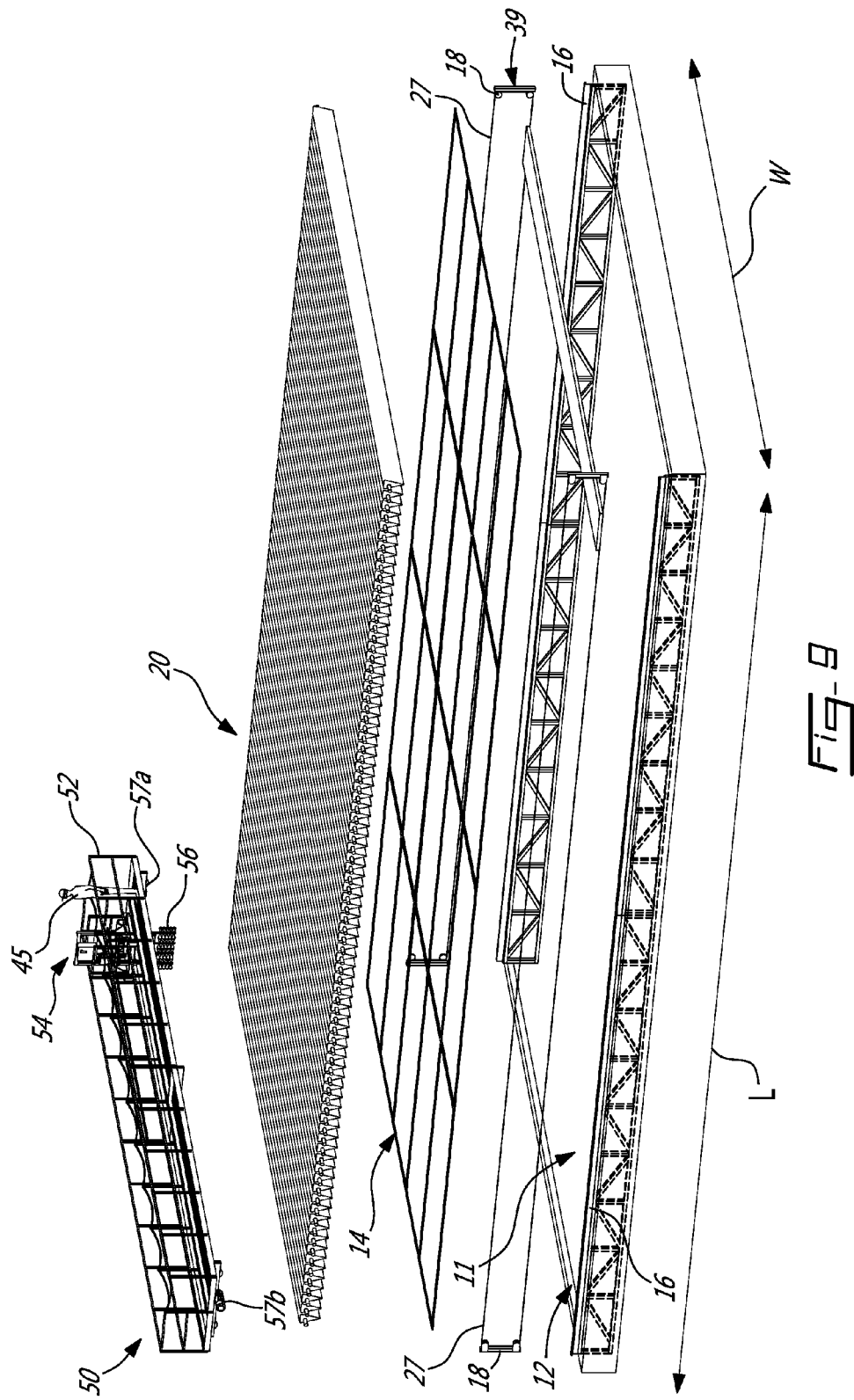

V-SHAPED LIGHT DISTRIBUTOR SYSTEM

CROSS-REFERENCE TO RELATED APPLICATIONS

The present application is related to U.S. patent application publication No. 2013/0219781 entitled "Sun tracking light distributor system" and to U.S. patent application publication No. 2013/0323713 entitled "Sun tracking light distributor system having a V-shaped light distribution channel", both of which are hereby incorporated by reference.

TECHNICAL FIELD

The present application relates to light distribution systems for use in open and closed photosynthetic culture aqueous systems that use the sun as a light source. The light distributors have a V-shaped light distribution surface to provide a distribution of the light in the aqueous volume. The light distributors are adapted to be oriented to track the sun.

BACKGROUND OF THE ART

Photosynthetic culture in aqueous liquids is often used for the production of algae. Two main types are known in the art, the open-ended systems such as ponds and basins and the closed systems such as photo-bioreactors (PBR). The aqueous liquid provided in the system typically includes water and the photosynthetic culture organisms such as algae or micro-organisms. It can include other substances.

Various configurations allow light to penetrate the aqueous liquid of the aqueous systems. However, these configurations either do not take into account the solar position throughout the day and throughout the year or can exhibit prohibitive optical losses or alignment precision requirements.

SUMMARY

According to one broad aspect of the present invention, there is provided a sun-tracking light distributor for use in one of an open-ended system and a closed photo-bioreactor for a photosynthetic culture having an aqueous liquid. The light distributor comprises two light distribution walls each having a top end and a bottom end, the two light distribution walls being connected at their bottom ends, the light distribution walls being made of a transparent material allowing sunlight to pass therethrough, the two converging light distribution walls creating an elongated V-shaped channel with an interior space adapted to receive the sunlight and an exterior surface adapted to be partly immersed in the aqueous liquid in use, wherein the sun-tracking light distributor has a center of buoyancy, a vertical passing through the center of buoyancy defines an axis of flotation, and a pivot point of the sun-tracking light distributor is offset relative to the axis of flotation of the sun-tracking light distributor.

In one embodiment, the pivot point is a point of connection adapted to pivotally connect the sun-tracking light distributor to a tank containing the aqueous liquid.

In one embodiment, the pivot point is a center of gravity of the sun-tracking light distributor.

According to another broad aspect of the present invention, there is provided a sun-tracking light distributor for a photosynthetic culture, comprising: two light distribution walls made of a transparent material, creating an elongated V-shaped channel adapted to receive the sunlight and to be partly immersed in the aqueous liquid, the sun-tracking light distributor has a center of buoyancy, a vertical passing through the center of buoyancy defines an axis of flotation, and a pivot point of the sun-tracking light distributor is offset relative to the axis of flotation.

According to another broad aspect of the present invention, there is provided a cleaning system for a plurality of adjacent elongated light distributors for use in one of an open-ended system and a closed photo-bioreactor for a photosynthetic culture having an aqueous liquid. The cleaning system comprises a mobile bridge disposed above the light distributors and movable from a first position relative to the light distributors to a second position relative to the light distributors; and a cleaning module operatively connected to the mobile bridge movable from a first position relative to the mobile bridge to a second position relative to the mobile bridge, such that when in operation, the mobile bridge and the cleaning module are adapted to be displaced over a surface area defined by a top of the light distributors, the cleaning module including a cleaning head, the cleaning head including at least one cleaning element, when in operation the cleaning element being at least partially immersed in the aqueous liquid and being disposed between two adjacent light distributors.

In one embodiment, the cleaning element is a prong including at least one aperture for delivering cleaning fluid to the two adjacent light distributors.

In one embodiment, the cleaning element includes at least one brush; and when in operation, the at least one brush being immersed and brushing a portion of a nearby light distributor.

According to another broad aspect of the present invention, there is provided a cleaning system for a plurality of adjacent elongated light distributors comprising: a mobile bridge and a cleaning module, adapted to be displaced over a surface area defined by a top of the light distributors, the cleaning module including a cleaning head, having at least one cleaning element, when in operation the cleaning element being at least partially immersed in the aqueous liquid and being disposed between two adjacent light distributors.

According to one broad aspect of the present invention, there is provided a sun-tracking light distributor for a photosynthetic culture in an aqueous liquid, comprising: two light distribution walls made of a transparent material, creating an elongated V-shaped channel adapted to receive the sunlight and to be partly immersed in the aqueous liquid, the sun-tracking light distributor having a center of buoyancy, a vertical passing through the center of buoyancy defining an axis of flotation, a pivot axis of the sun-tracking light distributor being offset relative to the axis of flotation. Owing to the offset pivot axis, the orientation of the light distributor is changed by varying the level of aqueous liquid, thus allowing a tracking of the sun's altitude.

According to still another broad aspect of the present invention, there is provided a sun-tracking light distributor system for use in a photosynthetic culture having an aqueous liquid contained in a tank, the sun-tracking light distributor system comprising: a light distributor having two elongated light distribution walls each having a top end and a bottom end, the two elongated light distribution walls converging and being connected at their bottom ends, the light distribution walls being made of a transparent material allowing sunlight to pass therethrough, the two converging light distribution walls creating an elongated V-shaped channel with an interior space adapted to receive the sunlight and an exterior surface adapted to be partly immersed in the aqueous liquid in use, the light distributor having a center of buoyancy, a vertical passing through the center of buoyancy defining an axis of flotation; and a pivot assembly for pivotally connecting the light distributor to at least one of two opposite sides of the tank, the pivot assembly defining a pivot axis for the light distributor, the pivot axis being offset relative to the axis of flotation of the light distributor, the pivot assembly causing a change in inclination of the light distributor in the tank in response to a change of level of the aqueous liquid in the tank.

In one embodiment, the light distributor further comprises a light entry surface wall joining the top ends of the light distribution walls, the light entry surface wall being made of a transparent material allowing sunlight to pass therethrough, the two converging light distribution walls and the light entry surface wall creating an enclosed elongated channel with a triangular cross-section.

In one embodiment, the sun-tracking light distributor system further comprises closing walls at longitudinal ends of the light distributor, the closing walls being rigidly attached to cross-sectional edges of the light distribution walls.

In one embodiment, the pivot assembly comprises a pivot shaft having a center axis, the center axis defining the pivot axis, the pivot shaft allowing a pivotal connection between the light distributor and the tank.

In one embodiment, the pivot assembly further includes an arm for the pivot shaft, the arm being adapted to locate the pivot axis outside of the interior space of the light distributor.

In one embodiment, the pivot assembly comprises a preload, the preload limiting a span of inclinations of the light distributor.

In one embodiment, the preload is selected from the group consisting of a torsion spring disposed around the pivot shaft, a mass attached to a preload arm rigidly connected to the pivot shaft, and a compression spring attached to a preload arm rigidly connected to the pivot shaft.

According to another broad aspect of the present invention, there is provided a method for distributing light in a photosynthetic culture, comprising: providing a sun-tracking light distributor system and changing the level of the aqueous liquid in the tank to cause the light distributor to be inclined to capture a portion of the sunlight.

BRIEF DESCRIPTION OF THE DRAWINGS

Having thus generally described the nature of the invention, reference will now be made to the accompanying drawings, showing by way of illustration example embodiments thereof and in which:

FIG. 1 is a perspective exploded view of a growth system including a tank, a network of delivery pipes and a plurality of V-shaped light distributors;

FIG. 2 includes FIG. 2A and FIG. 2B in which

FIG. 3 includes FIG. 3A and FIG. 3B which are cross-sectional views of one of the V-shaped light distributors of FIG. 1 at the vertical (FIG. 3A) and shown in a first inclination with respect to the vertical (FIG. 3B), wherein the first inclination is induced by the level of the aqueous liquid it is disposed in;

FIG. 4 is a graph of the angle of inclination of any of the V-shaped light distributors of FIG. 1 as a function of the level of the aqueous liquid it is disposed in;

FIG. 5 includes FIG. 5A and FIG. 5B in which FIG. 5A is a first embodiment of a pivot assembly for pivotal connection of one of the V-shaped light distributors of FIG. 1 to the tank of FIG. 1 resulting in inclination of the V-shaped light distributor as a function of the level of the aqueous liquid and FIG. 5B is a detail of the pivot assembly of FIG. 5A;

FIG. 6 includes FIG. 6A and FIG. 6B in which

FIG. 7 includes FIG. 7A and FIG. 7B in which FIG. 7A is a third embodiment of a pivot assembly for pivotal connection of one of the V-shaped light distributors of FIG. 1 to the tank of FIG. 1 resulting in inclination of the V-shaped light distributor as a function of the level of the aqueous liquid and FIG. 7B is a detail of the pivot assembly of FIG. 7A;

FIG. 8 includes FIG. 8A and FIG. 8B in which FIG. 8A is a fourth embodiment of a pivot assembly for pivotal connection of one of the V-shaped light distributors of FIG. 1 to the tank of FIG. 1 resulting in inclination of the V-shaped light distributor as a function of the level of the aqueous liquid and FIG. 8B is a detail of the pivot assembly of FIG. 8A;

FIG. 9 is a perspective view of the growth system of FIG. 1 with a cleaning system for cleaning the plurality of V-shaped light distributors of FIG. 1;

FIG. 11 includes FIG. 11A and FIG. 11B in which

It will be noted that throughout the appended drawings, like features are identified by like reference numerals.

DETAILED DESCRIPTION

Referring to FIG. 1, a growth system 10 for photosynthetic organisms is provided. The growth system 10 includes a tank 12 filled with aqueous liquid 11 containing a suspension of photosynthetic culture. The aqueous liquid 11 is water. The photosynthetic culture is algae. It is contemplated that the photosynthetic culture could include, in addition to or instead of algae, other species that use photosynthesis, such as microorganisms. The tank 12 includes a drain system (not shown), a control system (not shown), concrete foundations (not shown) around the tank 12, sand foundations (not shown) below the tank 12 and a waterproof membrane (not shown) covering the bottom surface of the tank 12.

In one example embodiment, a level E (shown in FIGS. 3 and 12) of the aqueous liquid 11 is at about 0.8 m (32 inches). A width W of the tank 12 is about 15 m (590 inches).

A length L of the tank 12 is about 25 m (984 inches). It is contemplated that the tank 12 could have dimensions other than the ones given above.

A network 14 of delivery pipes is disposed in the aqueous liquid. The delivery pipes could allow distribution of gas in the aqueous solution. For example, carbon dioxide ($CO_2$) is consumed by the algae during its growth. It is contemplated that the delivered gas could be one or more of carbon monoxide (CO), sulfur dioxide ($SO_2$), azote dioxide ($NO_2$), and carbonyl sulfide (COS), to name a few. Nutrients and other compositions could also be delivered to the algae production via the delivery pipes, in gaseous, liquid or solid phase. It is also contemplated that the network 14 of delivery pipes could be omitted.

A sun-tracking light distributor system is disposed in the growth system. The sun-tracking light distributor system comprises at least one V-shaped light distributor which receives and distributes sunlight in the aqueous liquid and a pivot assembly for causing a change in inclination of the V-shaped light distributor(s).

Figure 2A:
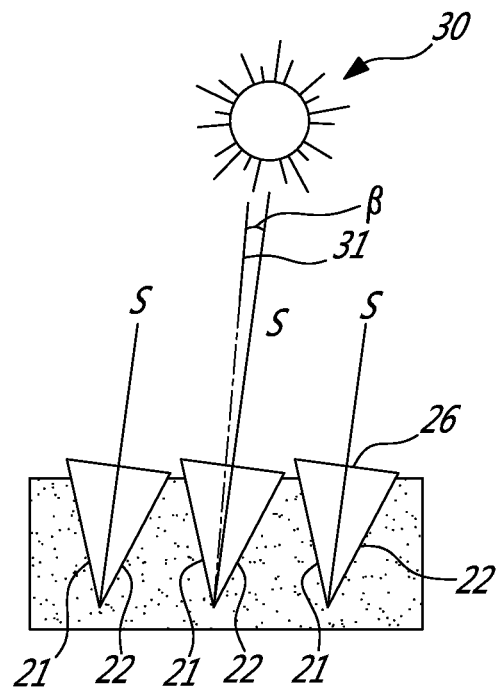
FIG. 2A is a cross-sectional view of three of the V-shaped light distributors of FIG. 1 receiving light from the sun, where the V-shaped light distributors have a first inclination with respect to the vertical
Figure 2B:
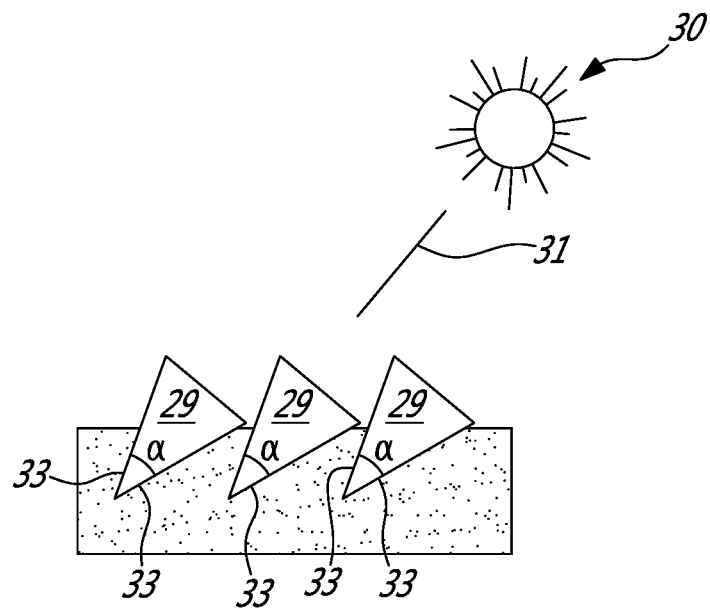
FIG. 2B is a cross-sectional view of the three V-shaped light distributors receiving light form the sun of FIG. 2A, where the V-shaped light distributors have a second inclination with respect to the vertical.

As shown in FIGS. 2A and 2B, a plurality of adjacent V-shaped light distributors 20 is provided at the interface between the air and the aqueous liquid 11. The V-shaped light distributors 20 are partially immersed in the aqueous liquid 11 and disposed above the network 14 of delivery pipes. The V-shaped light distributors 20 capture a part of the light coming from the sun 30 and distribute it within the aqueous liquid 11 down to a level deeper than what the sunlight would reach without the V-shaped light distributors 20 (i.e., deeper than the natural penetration depth of sunlight). For example, the penetration depth of sunlight in the volume where the V-shaped light distributors 20 are used can be 3 or even 5 to 10 times the natural penetration depth in the same aqueous liquid 11. By doing so, the V-shaped light distributors 20 accelerate photosynthesis of the algae by reaching algae than would otherwise be hidden from the sun 30 by those algae that are just below the surface of the aqueous liquid 11. The V-shaped light distributors 20 are disposed adjacent to each other so as to substantially cover the entire surface of the aqueous liquid 11.

Each of the V-shaped light distributors 20 has a longitudinal axis 24, as seen in FIG. 1. The longitudinal axis 24 is oriented East-West along the width W of the tank 12. Alternatively, the longitudinal axis 24 of the elongated V-shaped light distributors 20 could be oriented North-South. Other orientations are contemplated. The V-shaped light distributors 20 are pivotally connected to the opposite sides of the tank 12, either directly or indirectly through rails 16 disposed along the tank sides. The rails 16 ensure mutual alignment of the V-shaped light distributors 20.

In short, each light distributor has two elongated light distribution walls each having a top end and a bottom end. The two elongated light distribution walls converge and are connected at their bottom ends. The light distribution walls are made of a transparent material allowing sunlight to pass therethrough. The two converging light distribution walls create an elongated V-shaped channel with an interior space adapted to receive the sunlight and an exterior surface adapted to be partly immersed in the aqueous liquid in use. The light distributor has a center of buoyancy, an axis of flotation being defined by a vertical passing through the center of buoyancy.

Referring to FIGS. 2A and 2B, one of the light-tracking V-shaped light distributors 20 will now be described in detail. In this example embodiment, each of the plurality of adjacent V-shaped light distributors 20 is identical to the V-shaped light distributor 20 described below. It is contemplated, however, that some of the plurality of adjacent V-shaped light distributors 20 could differ from one another. The V-shaped light distributors 20 are light tracking, as their orientation is changed to follow the sun 30 depending on the season of the year. It is contemplated that the orientation of the V-shaped light distributors 20 could also follow the sun's daily path.

The V-shaped light distributor 20 includes left and right light distribution walls 21, 22 and a light entry surface wall 26, together forming a longitudinal structure having a hollow triangular cross-section. The walls 21, 22 are made of a transparent rigid plastic. It is contemplated that the walls 21, 22 could be made of a rigid, transparent material other than plastic. They could, for example, be made of Poly(methyl methacrylate) PMMA, polycarbonate or even glass. Although other manufacturing methods are contemplated, the walls 21, 22 are made by extrusion. In one example, the thickness of the walls 21, 22 is about 4 mm (0.15 inch). It is also contemplated that different portions of the walls 21, 22 could be made of different materials. For example, the upper part of the walls 21, 22 could be made of a material different from their lower part. The exterior surface 33 of the light distribution walls 21, 22 is adapted to be partially immersed in the tank 12. In another example, the V-shaped light distributor 20 has reinforcing portions, for example at its corners. The V-shaped light distributor 20 is designed to sustain the pressure from the aqueous liquid 11 that fills the tank 12 throughout the different seasons of the year.

The light distribution walls 21, 22 converge and are joined to each other at their lower ends so as to form a V-like structure that opens at an angle $\alpha$ (shown in FIG. 2B). The angle $\alpha$ can be of 10° to 40° for example. The light distribution walls 21, 22 are symmetric about an axis of symmetry S. It is contemplated however that the light distribution walls 21, 22 could not be symmetric, i.e., they are not necessarily identical. For example, the walls could have different transversal dimensions (heights). In another example, one wall could be curved or have angled sections along its transversal (or vertical) dimension. Curvatures or angled sections would not necessarily be present or mirrored in the other wall. In such a case, the axis of symmetry discussed herein would be replaced by an axis of reference disposed at mid-angle between the light distribution walls 21, 22. The light entry surface wall 26 joins the top ends of the distribution walls 21, 22 so as to form a longitudinal channel having a V-shaped (triangular) cross-section. The channel has an interior space 29 adapted to receive the sunlight.

When the V-shaped light distributor 20 is disposed in the tank 12, the light entry surface wall 26 is set slightly above the surface of the aqueous liquid 11 (as best shown in FIGS. 3A and 3B). The light entry surface wall 26 may be made of a polymer material having a low refractive index to lower the optical reflection losses. The light entry surface wall 26 may bear a light concentrator element (not shown) that allows propagating light through a channel that has a cross-section smaller than the light entry surface wall. A Fresnel lens is an example of such an optical component. Other example light concentrator elements include a standard converging lens of suitable focal length and a mirror (metallic or dielectric) disposed on the surface of the light distribution walls 21, 22. It is contemplated that the light entry surface wall 26 could be omitted and that the V-shaped light distributor 20 could be an open-top longitudinal V-shaped channel.

The surface area of the distribution walls 21, 22 exceeds that of the light entry surface wall 26. For example, the surface area of the distribution walls 21, 22 may be 3 times the size of the light entry surface wall 26. In another example, it may be 5 to 10 times the size of the light entry surface wall 26. In one example, the light entry surface wall 26 has a transverse width of 10-20 cm (about 4-8 inch). The light distribution walls 21, 22 have a height of about 30-50 cm (about 12-20 inches). The length of the light distribution walls 21, 22 along the longitudinal direction may depend on the rigidity of the materials used and of the structure created. For example, a V-shaped light distributor 20 can have a longitudinal length of 15 m (about 600 inches). The V-shaped light distributor 20 is filled with air at ambient pressure. It is contemplated that the interior space 29 of the V-shaped light distributor 20 could be filled with water to allow, for example, the V-shaped light distributor 20 to sink deeper in the tank 12. The interior space 29 could also be filled, partly or fully, with a transparent liquid or solid material to facilitate light propagation. Examples of such a material include ethanol, glycerol, or water. In cases where the selected material would fill the whole interior space 29, the density of the material is smaller than that of the aqueous liquid 11.

Although it cannot be shown in FIGS. 2 and 3, the longitudinal channel formed in the V-shaped light distributor 20 is closed at both ends with closing walls 23 rigidly attached to the cross-sectional edges of the light distribution walls 21, 22, and to the light entry surface wall 26, if this element is present. The closing walls 23 prevent the aqueous liquid 11 from penetrating into the interior space 29 of the channel or the transparent liquid material that could fill a part of the interior space 29 from flowing outside of the channel. The closing walls 23 can be made of a rigid plastic, which is not necessarily transparent. It is contemplated that the closing walls 23 can be made of another material. The use of closing walls 23 can be avoided in embodiments wherein whole interior space 29 would be filled with a solid material.

The axis of symmetry S (or the axis of reference disposed between the light distribution walls 21, 22 at a middle of the angle α should the V-shaped light distributor 20 not be symmetric) may be oriented at an angle β of between 5 and 15 degrees with respect to the propagation direction of the sun rays 31 when the sun 30 is at its highest altitude. Photosynthetic culture is known to require a light intensity lower than the available maximum solar light intensity. Studies have shown that optimal intensities for photosynthesis can be of the order of 10% of the maximum solar light intensity. Although the angle β is calculated when the sun 30 is at its maximum altitude, for the rest of the day, the sun rays 31 will be sufficiently well oriented to still be captured by the V-shaped light distributor 20 and distributed within the volume of aqueous liquid 11 while yielding light dilution factors higher than what prevails at the time of maximum sun altitude. In most situations, the orientation of the V-shaped light distributors 20 will not need to be changed during the day and can only be modified once a day or even once every few days, or even a few times a year. As will be readily understood, should one wish to adjust the orientation more often, it will be possible to do so using the pivot assembly described below. The tracking may be approximate, within a precision range acceptable for the application.

In short, the pivot assembly is for pivotally connecting the light distributor to at least one of two opposite sides of the tank. The pivot assembly defines a pivot axis for the light distributor. This pivot axis is offset relative to the axis of flotation of the light distributor. The pivot assembly causes a change in inclination of the light distributor in the tank in response to a change of level of the aqueous liquid in the tank.

Figure 4:
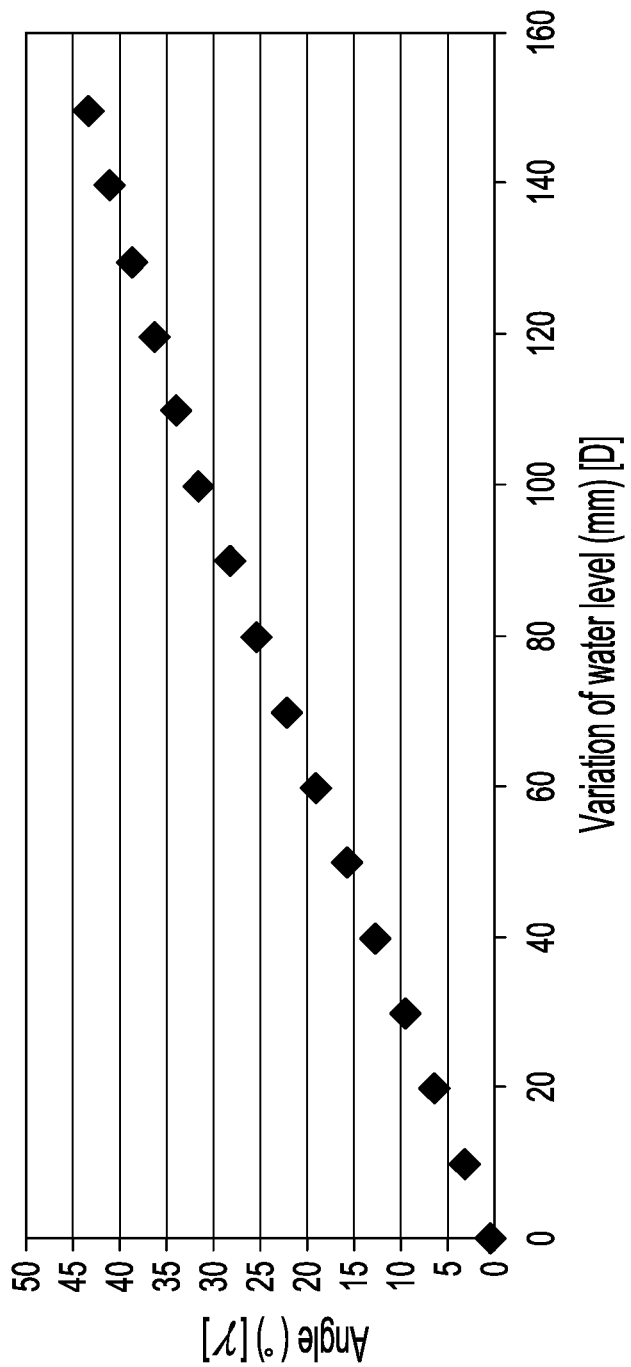

Turning to FIGS. 3 to 8B, the pivot assembly for adjusting the inclination of the V-shaped light distributor 20 with respect to the vertical V will now be described in detail. Referring more particularly to FIGS. 3 and 4, the pivot assembly operates by forcing the V-shaped shaped light distributor 20 to rotate about a longitudinally-extending pivot axis in response to a change of the level E of the aqueous liquid 11 in the tank 12. An orientation of the V-shaped light distributor 20 is defined by the angle γ between the axis of symmetry S (or axis of reference when the V-shaped light distributor 20 is not symmetric) and the vertical V.

The V-shaped light distributor 20 has a pivot axis PI that is offset (illustrated by the spacing labeled OFF in FIGS. 3A and 3B) with respect to an axis of flotation F of the V-shaped light distributor 20. By "offset" it is understood that the pivot axis PI does not intersect the axis of flotation F. The axis of flotation F is the vertical passing through the center of buoyancy ABF of the V-shaped light distributor 20. The center of buoyancy is the point where the buoyant force resulting from Archimedes' principle is applied. The pivot axis PI extends perpendicularly to the plane of FIGS. 3A and 3B.

In the example shown in the figures, the V-shaped light distributor 20 is symmetric and the axis of flotation F coincides with the axis of symmetry S when the V-shaped light distributor 20 is free floating and balanced (FIG. 3A). However, in cases where the V-shaped light distributor 20 is not symmetric (i.e., the light distribution walls 21, 22 are not symmetric to each other) and/or unbalanced, the axis of flotation F would be distinct from the axis of symmetry S. The pivot axis PI is chosen to be offset from the center of buoyancy ABF for any value of the angle of inclination γ (within the desired range) of the V-shaped light distributor 20. The calculation of the position of the center of buoyancy ABF can be carried out for any inclination angle of the structure. As will explained in further details below, the V-shaped light distributor 20 connects to the rails 16 mounted on the tank 12 by at least one shaft having its axis coincident with the pivot axis PI.

The offset OFF causes the buoyancy force to act as a lever and create a torque (illustrated by arrow T in FIG. 3B) on the V-shaped light distributor 20. A correlation between the angle γ and the level E of the aqueous liquid 11 in the tank 12 is shown in FIG. 4. The angle γ between the axis of symmetry S of the V-shaped light distributor 20 and the vertical V increases when the level E of the aqueous liquid 11 in the tank 12 decreases. In FIG. 4, the variation D of water level is defined with respect to the level at which the axis of symmetry S is vertical. An operator can thus modify the inclination of the V-shaped light distributor 20 depending on the time of the year by simply changing the level E of the aqueous liquid 11 in the tank 12. The change in level E of the aqueous liquid 11 can be controlled by introducing more aqueous liquid in the tank or removing some of the aqueous liquid from the tank. This can be done manually by an operator using a source of aqueous liquid, a pipe and/or a pump or can be partially or fully automated, for example via a control system controlling a pump having access to the source of aqueous liquid. It will be readily understood that additional pipes and valves could be provided to facilitate the change in level of the aqueous liquid. Sensors can be used to detect the position of the sun and commands can be issued to orient the light distributors automatically and accordingly. The controller can provide an actuation command for the actuator(s) which control the level of aqueous liquid in the tank. The controller may use stored solar position data to prepare the actuation command. For example, tables including the solar position for the time of day and day of year can be used by the controller. The controller may receive a manual input from a user to prepare the actuation command. The actuator(s) may also directly receive a manual input from a user to displace the light distributors. Feedback signals can be used to adjust the position and/or the position can be preprogrammed according to sun inclination projection data.

FIGS. 2A and 2B show different inclinations of the V-shaped light distributor 20 relevant for different times of the year and caused by different levels of aqueous liquid in the tank. A finite element model has shown that a variation D of about 150 mm (6 inches) could tilt the axis of symmetry S by an angle γ of 45°.

FIGS. 5A to 8B show examples of pivot assemblies or means for pivotally connecting the V-shaped light distributor 20 to the tank 12, where the pivot axis PI is offset relative to the axis of flotation F. For the sake of illustration, the tank 12 is depicted in FIGS. 5A to 8A with unrealistically small dimensions, selected to enclose a single unit of the V-shaped light distributors 20 with its pivot assembly.

In FIGS. 5A and 5B, the pivot axis PI of the V-shaped light distributor 20 is located outside of the interior space 29. It is contemplated that the pivot axis PI could be disposed inside of the interior space 29, as shown in FIGS. 3A and 3B. The pivot axis PI passes through an arm 19 fixed rigidly to a structural element of the V-shaped light distributor 20. This structural element could be the closing wall 23, and in this case the arm 19 protrudes from a side edge of the closing wall 23 while forming an integral part of this wall. Alternatively, the arm 19 could take the form of a member separate from the light distribution wall 22 and fixed rigidly to it. A pivot shaft 13 connects, via the arm 19, one end of the V-shaped light distributor 20 to one side of the tank 12 (or to the rails 16 when present as shown in FIG. 1). The center axis of the pivot shaft 13 defines the pivot axis PI of the V-shaped light distributor 20. The length of the arm 19 is determined by the desired span of inclinations of the V-shaped light distributor 20.

One of the pivot shaft 13 is fixedly connected to the arm 19 while the other end of the pivot shaft 13 engages in an opening properly machined in the tank sides (or through rails 16 shown in FIG. 1) such that the pivot shaft 13 can rotate with low friction about its axis. Alternatively, one end of the pivot shaft 13 can be fixedly connected to the tank sides (or through rails 16 shown in FIG. 1) while the other end connects to the arm 19 in such a way that a low-friction rotation of the pivot shaft 13 is provided. In another embodiment, a low-friction rotatable connection is provided at both ends of the pivot shaft 13.

It will be understood that the example embodiment illustrated in FIGS. 5A and 5B for pivoting the V-shaped light distributor 20 in response to a change in the level of the aqueous liquid 11 is generally present at both ends of the light distributor 20. It is contemplated, however, that the pivot assembly for pivoting the V-shaped light distributor 20 be present at only one end, particularly when the length of the light distributor 20 is kept short enough to avoid any excessive bending stress on the pivot shaft 13.

Figure 6B:
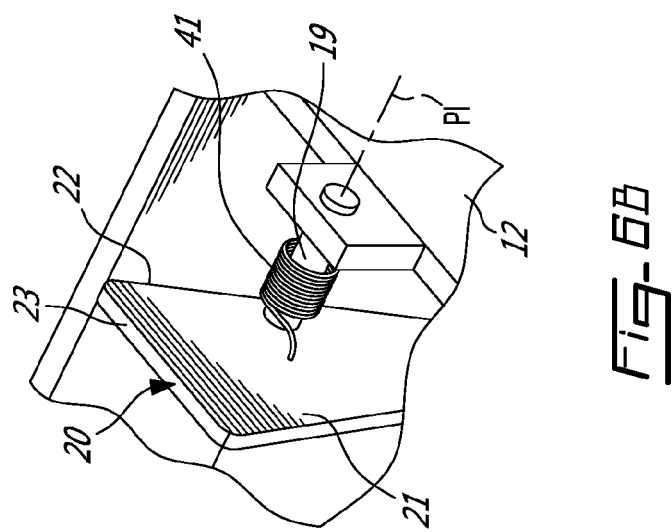
FIG. 6A is a second embodiment of a pivot assembly for pivotal connection of one of the V-shaped light distributors of FIG. 1 to the tank of FIG. 1 resulting in inclination of the V-shaped light distributor as a function of the level of the aqueous liquid and FIG. 6B is a detail of the pivot assembly of FIG. 6A.
Figure 6A:
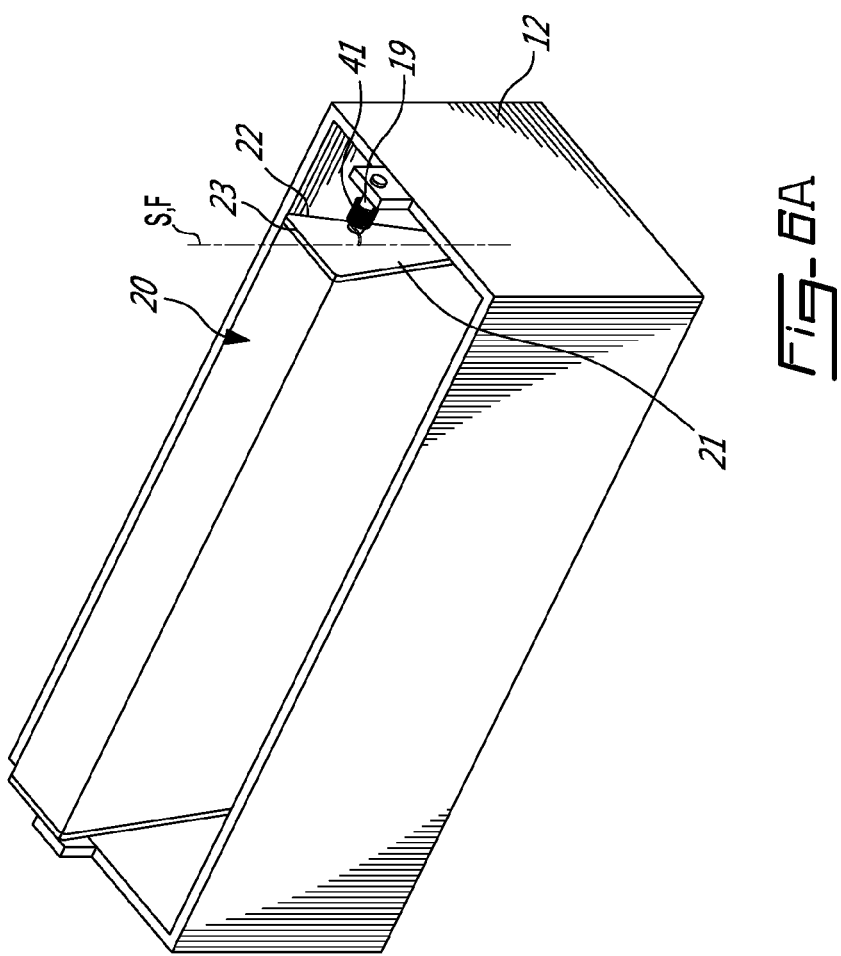

In FIGS. 6A and 6B, another embodiment of the pivot assembly is illustrated, in which the pivot axis PI is disposed inside of the interior space 29, so that no arm 19 is required. It is contemplated that the pivot axis PI could be disposed outside of the interior space 29, as shown FIG. 5A. A torsion spring 41 is disposed around the pivot shaft 13 pivotally linking the V-shaped light distributor 20 to the tank 12. The torsion spring 41 acts as a preload to control the desired span of inclinations γ of the V-shaped light distributor 20.

In FIGS. 7A and 7B, the pivot axis PI is disposed inside of the interior space 29. It is contemplated that the pivot axis PI could be disposed outside of the interior space 29, as shown FIG. 5A. A mass 43 is attached to one end of an arm 17, the other end of the arm 17 being secured to the pivot shaft 13. The mass 43 acts as a preload to control the desired span of inclinations of the V-shaped light distributor 20, just as the torsion spring 41 does in the embodiment illustrated in FIGS. 6A and 6B.

In FIGS. 8A and 8B, the pivot axis PI is disposed inside of the interior space 29. It is contemplated that the pivot axis PI could be disposed outside of the interior space 29, as shown FIG. 5A. A compression spring 47 has one end connected to the arm 17, which is connected to the pivot shaft 13, and another end connected to tank 12. The compression spring 47 acts as a preload to control the desired span of inclinations of the V-shaped light distributor 20, just as the torsion spring 41 and mass 43 do.

Preloads other than the ones shown in FIGS. 6A to 8B are also contemplated.

As will be readily understood, in order to distribute light in a photosynthetic culture, the sun-tracking light distributor system, comprising a light distributor and a pivot assembly, is provided in the growth system. Then, the level of the aqueous liquid in the tank is changed, as need be, to cause the light distributor to be inclined to capture a portion of the sunlight.

Turning now to FIGS. 9 to 12, a system 50 for cleaning the plurality of V-shaped light distributors 20 will be described. Algae and other contaminants can progressively accumulate on the light distribution walls 21, 22 of the V-shaped light distributors 20. This accumulation of algae can reduce the efficiency of the V-shaped light distributors 20 in distributing sunlight within the aqueous liquid 11. The cleaning system 50 allows the periodical removal of the algae from the light distribution walls 21, 22.

Figure 10:
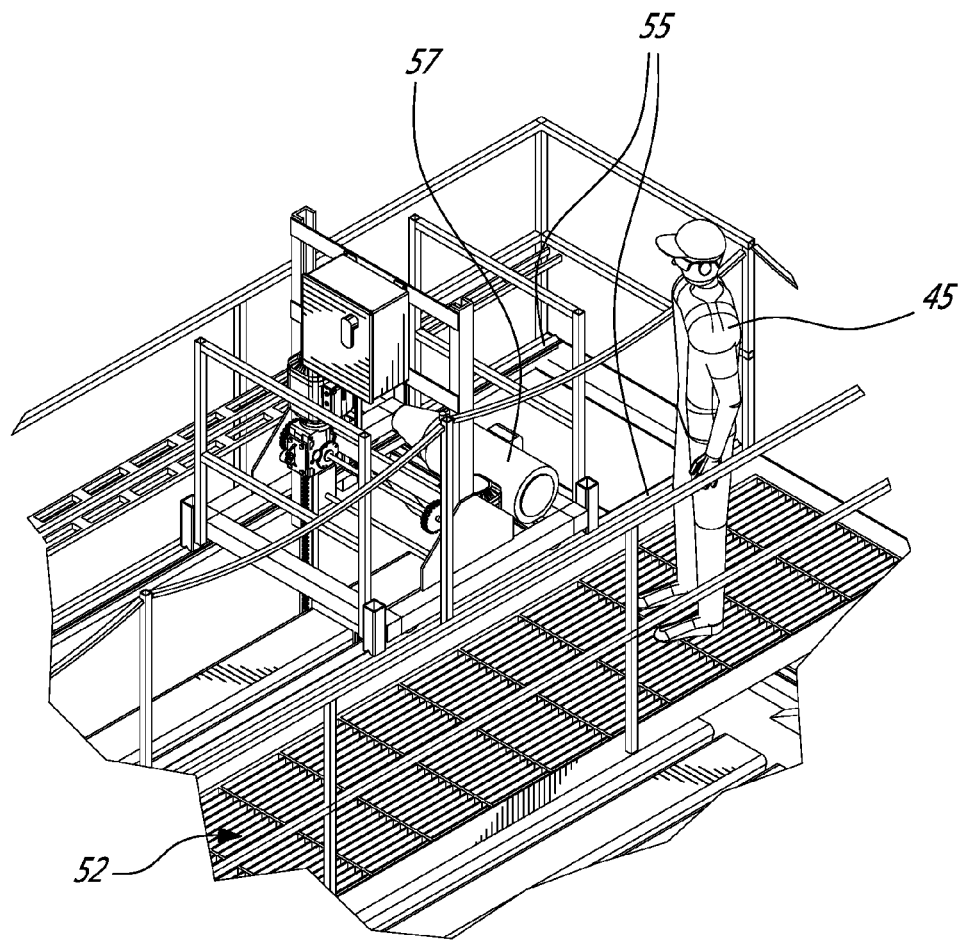
FIG. 10 is a zoom of a portion of the cleaning system of FIG. 9 revealing a portion of a cleaning module.
Figure 11B:
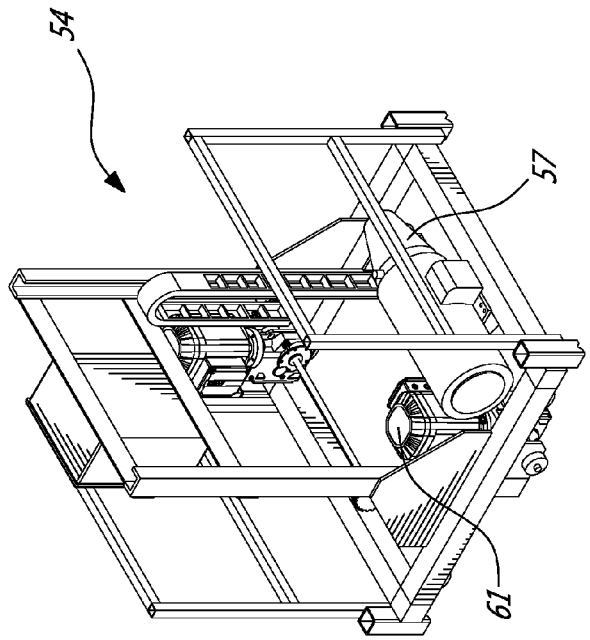
FIG. 11A is a perspective view of the cleaning module of FIG. 10 showing a cleaning head in an extended (or cleaning) position and FIG. 11B is a perspective view of the cleaning module of FIG. 10 showing the cleaning head in a retracted (or storage) position.
Figure 11A:
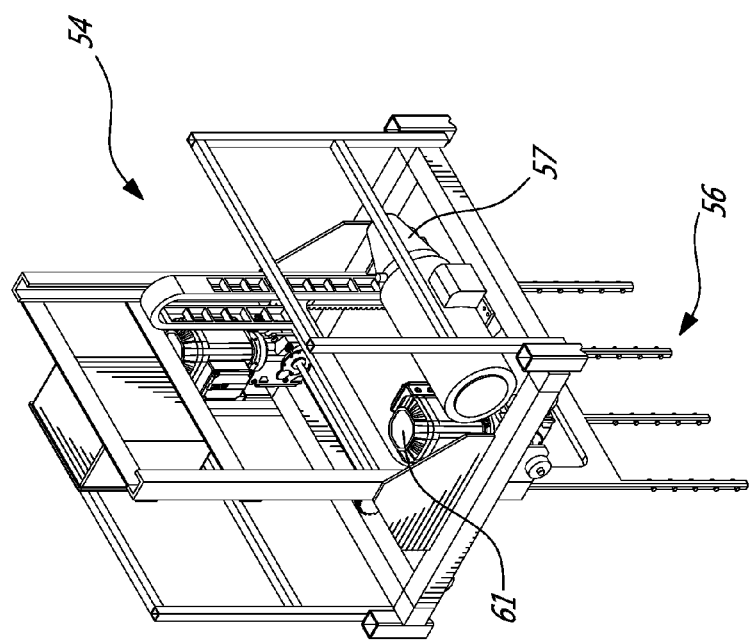

The cleaning system 50 includes a mobile bridge 52 provided with wheels 25 for moving on the rails 16 along the length L of the tank 12 using a driving unit 61 (shown in FIGS. 11A and 11B). The mobile bridge 52 is aligned with the longitudinal direction of the V-shaped light distributors 20, and is capable to sustain the weight of a couple of operators 45. The mobile bridge 52 may also be used for operations other than cleaning. For example, the mobile bridge 52 could be used for inspection of the V-shaped light distributors 20. Movably connected to a side of the mobile bridge 52 is a cleaning module 54. As shown in FIGS. 9 and 10, the cleaning module 54 travels along the length of the mobile bridge 52 along rails 55 using the driving unit 61. As such, the cleaning module 54 travels along the width W of the tank 12. It is contemplated that the mobile bridge 52 and the cleaning module 54 could have other orientations. For example, the mobile bridge 52 could be traveled along the width W of the tank 12, while the cleaning module 54 could travel along the length of the tank 12. An algae harvesting module 39 may be provided on the growth system 10, and also be made to travel using driving and guiding belts 27 cooperating with pulleys 18 and coupled to an appropriate driving unit (not shown).

The cleaning module 54 includes a cleaning head 56 movable vertically with respect to the mobile bridge 52. The cleaning head 56 is movable between two positions. FIG.

11A shows the cleaning head 56 in an extended position (or cleaning position), and FIG. 11B shows the cleaning head 56 in a retracted position (or storage position). In the extended position, the cleaning head 56 is immersed in the aqueous liquid 11 proximate to the light distribution walls 21, 22. In the retracted position, the cleaning head 56 is located distal from the V-shaped light distributors 20, which allows the mobile bridge 52 to be displaced without damaging the V-shaped light distributors 20. It is contemplated that the cleaning module 54 could be disposed directly beneath the mobile bridge 52.

The cleaning head 56 includes four prongs 58, each including a plurality of apertures 59 that deliver jets 60 of cleaning fluid toward the light distribution walls 21, 22 of the V-shaped light distributors 20. The cleaning fluid is the aqueous liquid 11 with some of the photosynthetic culture that is pumped directly from the tank 12. It is contemplated that the cleaning fluid could instead be water with or without a cleaning agent compatible with the photosynthetic culture. A pump 57 disposed on the cleaning module 54 ensures the pumping of the aqueous liquid 11 toward the cleaning head 56. It is contemplated that the pump 57 could be disposed elsewhere on the growth system 10. The cleaning head 56 is capable of cleaning simultaneously three of the V-shaped light distributors 20, an abutment wall 21 of an adjacent one of the V-shaped light distributors 20, and an abutment wall 22 of another adjacent one of the V-shaped light distributors 20. It is contemplated that the cleaning head 56 could clean simultaneously more or less than three of the V-shaped light distributors 20. It is contemplated that the cleaning head 56 could have, in addition to or in place of the prongs 58, one or more brushes to brush the algae or dirt that may have accumulated on the light distribution walls 21, 22 of the V-shaped light distributors 20. Each prong 58 could be provided with a guide having a slipping surface or with rollers to follow the inclination of distribution walls 21, 22.

Figure 12:
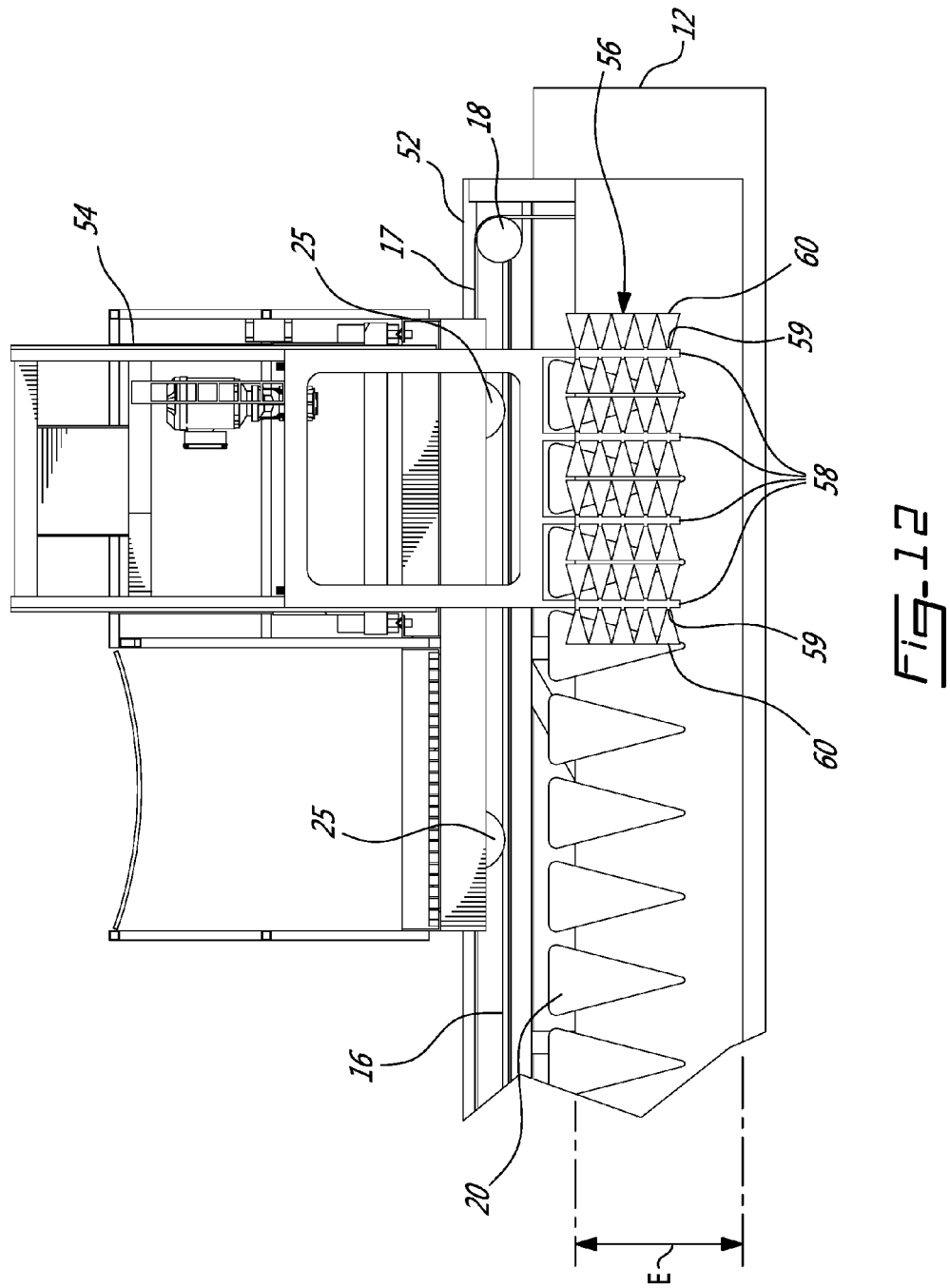
FIG. 12 is a cross-sectional view of the cleaning module of FIG. 10 with the cleaning head in the extended position and partially immersed in the tank of FIG. 1.

The cleaning system 50 works as follows. The operator first positions the mobile bridge 52 at one end of the tank 12 with the cleaning head 56 at a first end 57a of the mobile bridge 52. If this is not already done, the operator 45 sets the cleaning head 56 in extended position. In this position, as best seen in FIG. 12, the prongs 58 are disposed in-between adjacent V-shaped light distributors 20. As aqueous liquid 11 is being pumped from the tank 12 and delivered to the V-shaped light distributors 20, the cleaning head 56 is displaced at a constant speed toward the second end 57b of the mobile bridge 52 along the V-shaped light distributors 20. The speed may be adjustable depending on the level of algae or dirt accumulated on the light distribution walls. Once the cleaning head 56 has reached the second end 57b of the mobile bridge 52, the cleaning head 56 is put in retracted position and the mobile bridge 52 is moved over a distance corresponding to the length covered by the next set of four V-shaped light distributors 20 to be cleaned. The cleaning head 56 is then displaced from the second end 57b of the mobile bridge 52 back to the first end 57a. The above steps are repeated until the entirety of the V-shaped light distributors 20 are cleaned. The above cleaning sequence can be performed automatically or partially or wholly by the operator 45. It is also contemplated that the cleaning sequence could be different from the one described herein. For example, each time four V-shaped light distributors 20 are cleaned, the cleaning head 56 can be moved back to the first end 57a of the mobile bridge 52.

As will be readily understood, the jets 60 of cleaning fluid delivered toward the light distribution walls 21, 22 may be of a sufficient range for the span of inclinations of the light distributors 20. It may be necessary to temporarily block rotation of the light distributors about their pivot axis prior to activating the cleaning system. This will prevent adjacent rows of light distributors from contacting if the pressure from the prongs is sufficient to cause the light distributors to rotate about their pivot axis and will prevent damages to the light distributors and pivot assemblies.

The embodiments described above are intended to be exemplary only. The scope of the invention is therefore intended to be limited solely by the appended claims.

We claim:

1. A sun-tracking light distributor system for use in a photosynthetic culture having an aqueous liquid contained in a tank, the sun-tracking light distributor system comprising:
   a light distributor having two elongated light distribution walls each having a top end and a bottom end, the two elongated light distribution walls converging and being connected at theft bottom ends, the light distribution walls being made of a transparent material allowing sunlight to pass therethrough, the two converging light distribution walls creating an elongated V-shaped channel with an interior space adapted to receive the sunlight and an exterior surface adapted to be partly immersed in the aqueous liquid contained in the tank in use; and
   a pivot assembly pivotally connecting the light distributor to at least one of two opposite sides of the tank and configured for enabling said light distributor to pivot freely in response to a change of level of said aqueous liquid contained in the tank in use, said pivot resulting in a change in inclination of said light distributor, said pivot assembly defining a pivot axis for said light distributor, said pivot axis extending along said elongated V-shaped channel and being positioned so as to be offset relative to an axis of flotation of said light distributor for any inclination of said light distributor, said axis of flotation being a vertical axis passing through a center of buoyancy of said light distributor when partly immersed in said aqueous liquid contained in the tank in use.

2. The sun-tracking light distributor system of claim 1, wherein said light distributor further comprises a light entry surface wall joining the top ends of said light distribution walls, the light entry surface wall being made of a transparent material allowing sunlight to pass therethrough, the two converging light distribution walls and the light entry surface wall creating an enclosed elongated channel with a triangular cross-section.

3. The sun-tracking light distributor system of claim 1, further comprising closing walls at longitudinal ends of said light distributor, said closing walls being rigidly attached to cross-sectional edges of said light distribution walls.

4. The sun-tracking light distributor system of claim 1, wherein said pivot assembly comprises a pivot shaft having a center axis, said center axis defining the pivot axis, said pivot shaft allowing a pivotal connection between said light distributor and said tank.

5. The sun-tracking light distributor system of claim 4, wherein said pivot assembly further includes an arm for said pivot shaft, said arm being adapted to locate the pivot axis outside of the interior space of the light distributor.

6. The sun-tracking light distributor system of claim 4, wherein the pivot assembly comprises a preload, said preload limiting a span of inclinations of the light distributor.

7. The sun-tracking light distributor system of claim 6, wherein the preload is selected from the group consisting of a torsion spring disposed around the pivot shaft, a mass attached to a preload arm rigidly connected to the pivot shaft, and a compression spring attached to a preload arm rigidly connected to the pivot shaft.

8. A method for distributing light in a photosynthetic culture having an aqueous liquid contained in a tank, the method comprising the steps of:

providing a sun-tracking light distributor system including:

a light distributor having two elongated light distribution walls each having a top end and a bottom end, the two elongated light distribution walls converging and being connected at their bottom ends, the light distribution walls being made of a transparent material allowing sunlight to pass therethrough, the two converging light distribution walls creating an elongated V-shaped channel with an interior space adapted to receive the sunlight and an exterior surface adapted to be partly immersed in the aqueous liquid contained in the tank; and a pivot assembly pivotally connecting the light distributor to at least one of two opposite sides of the tank and configured for enabling said light distributor to pivot freely in response to a change of level of said aqueous liquid contained in the tank, said pivot resulting in a change in inclination of said light distributor, said pivot assembly defining a pivot axis for said light distributor, said pivot axis extending along said elongated V-shaped channel and being positioned so as to be offset relative to an axis of flotation of said light distributor for any inclination of said light distributor, said axis of flotation being a vertical axis passing through a center of buoyancy of said light distributor when partly immersed in said aqueous liquid contained in the tank; and changing said level of said aqueous liquid in said tank to cause said light distributor to be inclined to capture a portion of said sunlight.

* * * * *

UNITED STATES PATENT AND TRADEMARK OFFICE
CERTIFICATE OF CORRECTION

PATENT NO. : 9,885,011 B2
APPLICATION NO. : 14/894353
DATED : February 6, 2018
INVENTOR(S) : Denis Hotte et al.

Page 1 of 1

It is certified that error appears in the above-identified patent and that said Letters Patent is hereby corrected as shown below:

In the Claims

Column 12, Line 18, cancel the text "connected at theft bottom ends" and insert the following text:
--connected at their bottom ends--

Signed and Sealed this
First Day of May, 2018

Andrei Iancu
*Director of the United States Patent and Trademark Office*